United States Patent
Le Hir et al.

(10) Patent No.: US 9,556,464 B2
(45) Date of Patent: Jan. 31, 2017

(54) **METHOD FOR PRODUCING *HAEMOPHILUS INFLUENZAE* TYPE B ANTIGENS**

(71) Applicant: Sanofi Pasteur, Lyons (FR)

(72) Inventors: Jérome Le Hir, Toulouse (FR); Pascal Loubiere, Donneville (FR); Fabien Barbirato, Brignais (FR); Nicholas Lindley, Parisot (FR)

(73) Assignee: Sanofi Pasteur, Lyons (FR)

( * ) Notice: Subject to any disclaimer, the term of this patent is extended or adjusted under 35 U.S.C. 154(b) by 0 days.

(21) Appl. No.: 14/411,241

(22) PCT Filed: Jul. 2, 2013

(86) PCT No.: PCT/FR2013/051549
§ 371 (c)(1),
(2) Date: Dec. 24, 2014

(87) PCT Pub. No.: WO2014/006318
PCT Pub. Date: Jan. 9, 2014

(65) Prior Publication Data
US 2015/0167036 A1    Jun. 18, 2015

(30) Foreign Application Priority Data
Jul. 2, 2012 (FR) .................... 12 56329

(51) Int. Cl.
| | | |
|---|---|---|
| C12N 1/20 | (2006.01) | |
| C12P 19/04 | (2006.01) | |
| A61K 39/102 | (2006.01) | |
| A61K 39/00 | (2006.01) | |

(52) U.S. Cl.
CPC .............. *C12P 19/04* (2013.01); *A61K 39/102* (2013.01); *C12N 1/20* (2013.01); *A61K 2039/6037* (2013.01)

(58) Field of Classification Search
None
See application file for complete search history.

(56) References Cited

FOREIGN PATENT DOCUMENTS

| WO | 00/56365 A1 | 9/2000 |
| WO | 2009/007641 A2 | 1/2009 |
| WO | 2009/081276 A2 | 7/2009 |

OTHER PUBLICATIONS

Todar (Online Textbook of Bacteriology. 2008-2012. Nutrition and Growth of Bacteria. Chapter 4; http://textbookofbacteriology.net/nutgro.html).*
McDevitt (PLoS Pathog. Nov. 2011; 7(11): 1-9. e1002357. published online Nov. 2011).*
Merritt et al., "Development and scale-up of a fed-batch process for the production of capsular polysaccharide from Haemophilus influenzae", Journal of Biotechnology, 2000, 81(2-3), 189-197.
Yeruva et al., "Screening of Medium Components for Polyribosyl Ribitol Phosphate Production by Haemophilus Influenzae Type-B Using Plackett-Burman Design", Journal of Cell and Tissue Research, 2010, 10(3), 2349-2352.
Jun et al., "Proteomic expression profiling of Haemophilus influenzae grown in pooled human sputum from adults with chronic obstructive pulmonary disease reveal antioxidant and stress responses", BMC Microbiology, 2010, 10(1), p. 162.

* cited by examiner

*Primary Examiner* — Jennifer Graser
(74) *Attorney, Agent, or Firm* — McDonnell Boehnen Hulbert & Berghoff LLP

(57) ABSTRACT

The invention concerns a method for producing, on an industrial scale, capsular polysaccharide of *Haemophilus influenzae* type b (PRP) intended for vaccine purposes, according to which a strain of *Haemophilus influenzae* type b (Hib) is cultured in a culture medium, the culture supernatant is harvested and treated in order to extract the capsular polysaccharide therefrom, said culture medium comprising at least: —one source of carbon, —protoporphyrin, —salts, —amino acids, —NAD or NADH, —vitamins, —means for regulating the pH, characterised in that said culture medium is chemically defined.

26 Claims, 1 Drawing Sheet

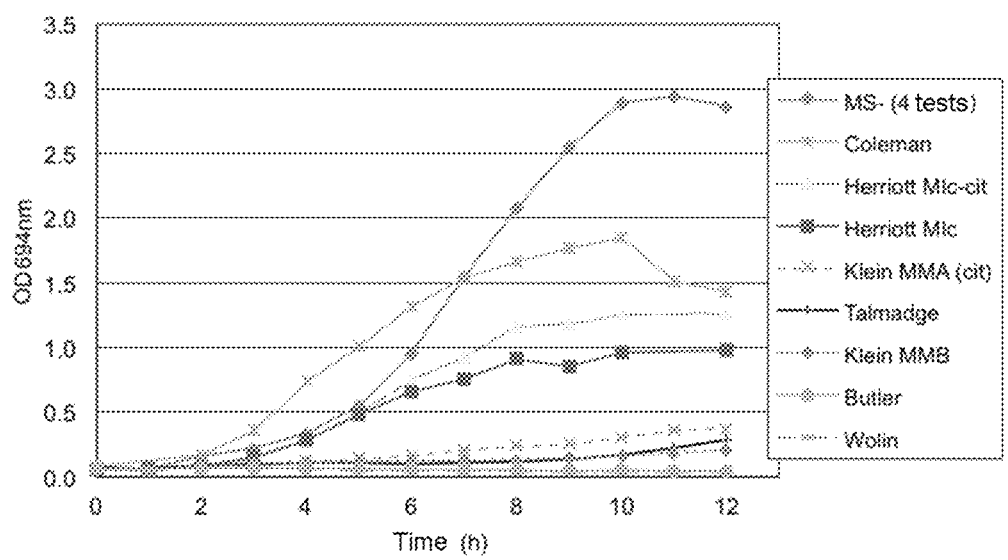

METHOD FOR PRODUCING *HAEMOPHILUS INFLUENZAE* TYPE B ANTIGENS

This application is a US national phase of International Application No. PCT/FR2013/051549 filed on Jul. 2, 2013, which claims priority to French Patent Application No. 1256329 filed on Jul. 2, 2012.

The present invention relates to a process for producing, on an industrial scale, capsular polysaccharides of *Haemophilus influenzae* type b (Hib), according to which a strain of Hib is cultured in a particular culture medium, the composition of which is chemically defined and which therefore comprises no complex source of nitrogen or of carbon. The prior art, and in particular application W2009/007641, describes improved culture media for *Haemophilus influenzae* type b, which do not comprise any element from an animal source, as is recommended when the purpose of the culture of *Haemophilus influenzae* type b is to produce capsular polysaccharide which will subsequently be introduced as an antigen into the composition of a vaccine. In the media described in this prior art, the source of nitrogen usually consisting of animal peptones is replaced with plant peptones.

Such media represent great progress in terms of the safety of pharmaceutical products with regard in particular to the elimination of the risk of transmission of diseases such as bovine spongiform encephalitis; they therefore make it possible to comply with Health Authority recommendations.

However, the composition of the peptones can vary according to the batches provided, which can lead to variations in the amounts of bacteria produced and also in the yields of antigens of interest, which vaccine producers try to limit or to correct by modifying certain parameters during the implementation of the process. However, in the context of the industrial production of a pharmaceutical product, it is desirable to be able to have available robust processes which require as few modifications as possible at each implementation, and the results of which at each step are reproducible from one batch to another.

Such processes must also allow yields that are compatible with industrial profitability, the criterion not being, in the case of production of antigens from bacteria, to obtain solely the largest possible amount of bacteria, but also to obtain the best ratio between the antigen titer and the amount of bacteria produced; it is therefore desirable for the bacterium to be cultured under conditions which direct its metabolism toward the production of capsular polysaccharide.

To this end, a subject of the present invention is a process for producing, on an industrial scale, capsular polysaccharide of *Haemophilus influenzae* type b (PRP) intended for vaccine purposes, according to which a strain of *Haemophilus influenzae* type b (Hib) is cultured in a culture medium, and the culture supernatant is harvested and treated in order to extract the capsular polysaccharide therefrom, said culture medium comprising at least:

one source of carbon,
protoporphyrin,
salts,
amino acids,
NAD or NADH,
vitamins,
pH-regulating means, characterized in that said culture medium is chemically defined.

By virtue of the invention, it is possible both to have a robust industrial process and to increase the production of capsular polysaccharide, without having to increase the biomass accordingly, thereby making it possible to reduce the amount of lipopolysaccharides (LPSs) produced relative to the amount of PRP produced.

In addition, the absence of proteins in the composition of the culture medium reduces the required needs in terms of antifoam product and simplifies the purification step which makes it possible, from the culture supernatant, to obtain the antigen consisting of the capsular polysaccharide.

According to the invention, the culture medium comprises pH-regulating means. These pH-regulating means can consist of buffer salts and/or of pH-measuring means combined with means for adding either an acid or a base to the medium. The yields can be optimized through the regulation of the pH.

According to one embodiment, the process according to the invention also consists in conjugating the PRP produced to a carrier protein, such as the tetanus protein.

A subject of the invention is also a process for preparing a vaccine composition, according to which:

an antigen against *Haemophilus influenzae* type b (Hib), consisting of the capsular polysaccharide (PRP), is prepared, on an industrial scale, by culturing a strain of Hib in a chemically defined medium of which the nature and the amount of each of the constituents is perfectly defined and which comprises at least:
one source of carbon,
protoporphyrin,
salts,
amino acids,
NAD or NADH,
vitamins,
and also pH-regulating means, the culture supernatant is harvested and treated in order to extract the purified capsular polysaccharide therefrom, the capsular polysaccharide is conjugated to a carrier protein.

According to one embodiment, the conjugate obtained is also combined with at least one or more antigens intended for vaccination against one or more of the following infections: diphtheria, tetanus, polio, hepatitis B, chicken pox, mumps, rubella, infections caused by *Neisseria meningitidis* or *Streptococcus pneumoniae*, infections caused by rotavirus, in order to obtain a vaccine combination which allows simultaneous immunization against several diseases.

According to the invention, the culture medium is chemically defined, i.e. the chemical structure and also the amount of each of the constituents are known. Such a medium is free of complex source of nitrogen or of carbon, such as peptones, caseins, sera or the like, and can therefore, if desired, be guaranteed to contain no element directly originating from an animal.

The invention relates to a process for producing, on an industrial scale, capsular polysaccharide of *Haemophilus influenzae* type b. Such a process makes it possible to obtain yields of biomass and of capsular polysaccharides or PRPs which are compatible with industrial constraints. Such a process makes it possible in particular to obtain, from a strain of *Haemophilus influenzae* type b which has in its genetic code at least 2 copies of the cap locus encoding the functions enabling capsular synthesis, without particular regulation of the medium (such as pH or $pO_2$), a biomass corresponding to an O.D. at 694 nm of at least 2.4 , after 12 hours of culture, and an associated amount of PRP of at least 240 mg/liter of culture medium. The determination of the amount of PRP produced is measured by means of a high-performance anion exchange chromatography with pulsed amperometric detection (HPAEC-PAD) technique (Dionex), or a method which gives equivalent results. Advantageously, the process according to the invention makes it possible to obtain an amount of PRP of at least 270 mg/liter of medium, and even more advantageously an amount of at least 300 mg/liter.

Among the possible sources for the carbon, mention may be made of all those which can be metabolized by the strain of *Haemophilus influenzae* type b, and in particular: glucose, fructose, galactose, glycerol, xylose, ribose, fucose, sialic acid and lactate. It is also possible to use 2 or more different sources, in particular lactate and glucose. According to the invention, the amount of glucose present in the starting medium is between 5 and 25 g/l, more particularly from 10 to 20 g/l, and more particularly from 12 to 16 g/l.

The amount of lactate present in the starting medium may be between 0 and 15 g/l, and more particularly from 0.5 to 10 g/l.

According to one embodiment of the invention, the protoporphyrin of the medium is synthetic protoporphyrin, for example the one provided by the company Sigma-Aldrich under reference 258385 (Protoporphyrin disodium salt). Thus, it is possible to use a medium that can be guaranteed to be completely free of substance of animal origin. Alternatively, synthetic protoporphyrin IX is used, the formula of which is the following:

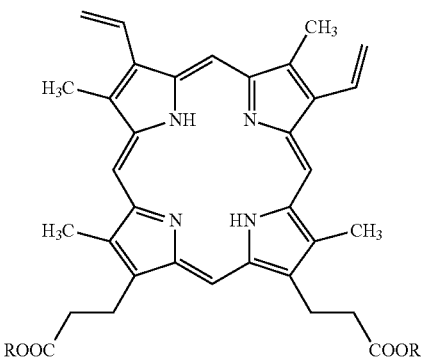

where R denotes H, or a counterion, preferably a counterion of an alkali metal, in particular sodium.

Such a protoporphyrin IX, and the method for preparing same, have been described in patent application FR 2 914 302.

According to the invention, the amount of protoporphyrin present in the starting medium is advantageously between 0.1 and 10 mg/l, and more particularly between 0.25 and 2 mg/l.

The culture medium according to the invention comprises salts which provide the minerals necessary for cell growth, which make it possible to ensure an osmotic pressure favorable to the bacteria, and which also exert a buffering capacity on the pH. Preferably, use is made of a mixture of monovalent cations such as $Na^+$ and/or $K^+$, of divalent cations such as $Ca^{++}$, $Mg^{++}$, $Co^{++}$, $Zn^{++}$, $Mn^{++}$, $Fe^{++}$, of phosphate anions in $HPO_4^{--}$, $H_2PO_4^-$ and/or $PO4^{--}$ form and of $SO_4^{--}$ and $Cl^-$ anions in the form of saline solutions, the molarities of each of which can usually vary within a concentration range of from $10^{-4}$ mM to 1000 mM.

The salts present in the culture medium are in particular chosen from:
$K_2HPO_4$; $KH_2PO_4$; $MgSO_4.7H_2O$; $Na_2HPO_4.12H_2O$; $NaH_2PO_4.2H_2O$; $CaCl_2.2H_2O$; $FeSO_4.7H_2O$; $ZnSO_4.7H_2O$; $CoCl_2.6H_2O$; $MnSO_4.H_2O$.

The salt concentrations are chosen in order to have an osmolarity of between 200 and 700 milliosmol/l, in particular between 300 and 400 milliosmol/l, especially 350 milliosmol/l, and a pH ranging from 6.5 to 7.5.

For this, the culture medium according to the invention can comprise in particular:
$MgSO_4.7H_2O$ at a concentration of between 150 and 1500 mg/l,
$CaCl_2.2H_2O$ at a concentration of between 6.5 and 52 mg/l,
$FeSO_4.7H_2O$ at a concentration of between 1.25 and 10 mg/l,
$ZnSO_4.7H_2O$ at a concentration of between 2.5 and 80 mg/l,
$CoCl_2.6H_2O$ between 0.5 and 2 mg/l,
$MnSO_4.H_2O$ between 2.5 and 10 mg/l,
sodium in the form in particular of sodium lactate at 60% in an amount of between 0 and 4 ml/l,
$K_2HPO_4$ and $KH_2PO_4$ at a concentration of, for each of them, between 100 and 1200 mg/liter when the buffer effect is provided by $Na_2HPO_4.12H_2O$/ $NaH_2PO_4.2H_2O$,
$Na_2HPO_4.12H_2O$ at a concentration of between 15 and 120 g/l,
$NaH_2PO_4.2H_2O$ at a concentration from 10 to 30 times lower than $Na_2HPO_4.12H_2O$.

Alternatively, it is possible for the buffer effect to be provided by the pair $K_2HPO_4$/$KH_2PO_4$; in this case, the $K_2HPO_4$ concentration is between 15 and 120 g/l, and the $KH_2PO_4$ concentration is from 10 to 30 times lower than that of $K_2HPO_4$; the concentration of $Na_2HPO_4.12H_2O$ and of $NaH_2PO_4.2H_2O$ can then be between 100 and 1200 mg/liter.

Among the salts mentioned, it has been possible to note that the presence of zinc is particularly advantageous for the production of biomass and of PRP, in particular in a concentration ranging from 2.5 to 80 mg/l, or more particularly from 5 to 20 mg/l. Very good results have been obtained at a concentration of 20 mg/l.

In the case where the pH of the culture medium is regulated during the culture phase, by the addition in particular of a highly concentrated base such as NaOH or KOH, it is possible to reduce the amount of salts present in the medium, and in particular the amount of the buffer pairs $Na_2HPO_4$/$NaH_2PO_4$, or $K_2HPO_4$/$KH_2PO_4$, provided, however, that the osmolarity is maintained at a suitable value, i.e. between 200 and 700 mOsm/l, through an optional addition of NaCl.

According to the invention, the culture medium also comprises NAD or a source of NAD, or of any other equivalent coenzyme. NAD (or β-nicotinamide adenine dinucleotide), also called coenzyme I or factor V, is a growth factor essential to the culture of *Haemophilus influenzae* type b. It is advantageously present at a concentration of between 0.5 and 50 mg/l, and more particularly between 2 and 10 mg/l, in particular 5 mg/l of culture medium. It can be introduced into the medium in its NADH reduced form. Alternatively to NAD, the culture medium according to the invention can comprise NAD precursor elements that the bacteria will be capable of using, such as NADP/NADPH (β-nicotinamide adenine dinucleotide phosphate) or NMN (β-nicotinamide adenine mononucleotide) or NR (nicotinamide riboside), 3-acetylpyridine adenine dinucleotide (APAD) or 3-acetylpyridine mononucleotide (APMN).

According to the invention, the culture medium contains amino acids which are advantageously chosen from: arginine, alanine, lysine, histidine, tryptophan, valine, isoleucine, leucine, tyrosine, phenylalanine, cystine (or an equivalent), asparagine, glutamine, aspartic acid and glutamic acid.

One formulation of the culture medium according to the invention comprises arginine, alanine, histidine, tryptophan, tyrosine, phenylalanine, cystine, aspartic acid and glutamic acid only. Alternatively, all of the amino acids mentioned are present in the culture medium.

According to one particular mode of the invention, the cystine is replaced with glutathione or cysteine.

According to one preferred embodiment, the process according to the invention uses a culture medium free of the following amino acids: L-methionine, L-glycine, L-proline, L-serine and L-threonine. This is because the presence of these amino acids resulted in an increase in the biomass, but not in a corresponding increase in PRP production. The amino acids are supplied in the form of very pure powders supplied by Sigma. Particularly advantageously, these amino acids have a synthetic origin or have been obtained by virtue of processes which guarantee the fact that they contain no element originating directly from an animal, in order to exclude any risk of contamination by transmissible infections, and in particular by BSE (Bovine Spongiform Encephalitis).

The amounts of each amino acid are chosen in order to optimize cell growth and PRP production. The amounts of aspartic acid, of asparagine and of glutamine are chosen so as to cause a deficiency during the cell culture, thereby making it possible to direct the metabolism of the cell towards the production of capsular polysaccharide, while the amounts of the other amino acids are chosen such that there is no deficiency during the culture phase.

According to the invention, the culture medium also contains vitamins which are chosen from: thiamine, pantothenate, uracil, hypoxanthine, biotin, riboflavin and pyridoxine.

For the purposes of the invention, the term "vitamins" also encompasses uracil and hypoxanthine which are nitrogenous bases.

Particularly advantageously, the vitamins present in the culture medium according to the invention have a non-animal origin, in particular a synthetic origin, thereby making it possible to exclude any risk of contamination by transmissible infections, and in particular by BSE (Bovine Spongiform Encephalitis). Use is in particular made of vitamins supplied by Sigma, the degree of purity of which is accurately known, thereby enabling a very accurate dosage during the preparation of the culture medium.

The amounts of vitamins present in the medium are chosen in order to optimize the production of biomass and of PRP.

According to one particular mode of the invention, the culture medium comprises citrulline which can substitute for arginine and for uracil.

In this case, the amount of citrulline included in the culture medium is advantageously between 150 and 500 mg/l.

By virtue of the culture medium according to the invention, it has been possible to produce Polyribosyl Ribitol Phosphate in greater amount than when media according to the prior art are used, while at the same not consuming more carbohydrate, and not producing more contaminant, in particular LPS.

According to one embodiment of the invention, the strain of *Haemophilus influenzae* type b cultured is an encapsulated strain which has at least 2 copies of the cap locus in its genetic code. This cap locus, between 17 and 18 kb in size, groups together genes of which the expression is linked to the synthesis and the exportation of the capsule.

The expression of the capsule gives the bacteria a white color when it is cultured on specific agar; the colonies of bacteria which have this cap locus are consequently called "white colonies", whereas the bacteria which do not export the capsular polysaccharide to the surface of the capsule are called "gray colonies". The expression of the capsule is subject to potential genetic instability, which can lead to the appearance of capsule-deficient mutants, which would consequently lead to a decrease in PRP production. Studies have made it possible to demonstrate that the chemically defined medium used in the process according to the invention makes it possible to ensure good genetic stability of the strain used during about twenty cell generations.

According to the invention, it is possible to perform the culture of the *Haemophilus influenzae* type b bacterium in several successive steps so as to gradually increase the biomass.

In this case, the bacteria originating from a lyophilisate or from a frozen sample are inoculated into a volume of medium which generally does not exceed 1 liter. After culture overnight or when the optical density of the medium is sufficient, this first culture is transferred into a second culture medium identical to the first, but the volume of which may be up to 10 to 20 times greater. The amount of bacteria inoculated into the second medium is adjusted such that the initial optical density (O.D.) of the second culture medium at 694 nm is between 0.2 and 0.4 so as to promote rapid growth of the bacterial population. This second culture is usually performed in a fermentor, but other types of containers can be used (flasks, spinners, etc). When the culture is performed in a fermentor, a temperature of 37° C.+/−1° C., constant stirring, a pressure of 0.1 bar, a $pO_2$ of 30% and an air flow rate of 0.25 volume of gas per volume of medium per minute are normally used for the duration of the culture. It is within the competence of those skilled in the art to choose other parameters for this type of culture. At the end of the exponential bacterial growth phase, the biomass can be further amplified by transferring it into another fermentor of larger capacity using the same procedure and so on. The culture volumes obtained can reach, or even exceed, 1000 liters. The culture(s) is (are) generally performed according to the "batchwise" mode.

Finally, the supernatant of the final culture is taken after inactivation of the bacteria. The inactivation is conventionally carried out using a solution of formol at a final concentration of 0.35%-0.37% (V/V). The supernatant is conventionally separated from the bacteria by means of a centrifugation step. The PRP contained in the resulting supernatant is then extracted and purified according to conventional processes well known to those skilled in the art.

The PRP harvested and purified is then advantageously conjugated to a carrier protein such as the tetanus protein, in order to make it T-dependent and to enable in particular the immunization of young children. The PRP-T antigen thus obtained can then be used alone in a monovalent vaccine, or be combined with other antigens in order to enable simultaneous vaccination against several diseases.

Particularly advantageously, the present invention provides a process for preparing a vaccine composition, according to which the conjugate obtained is combined with at least one or more antigens usually present in pediatric vaccines, and in particular antigens against diphtheria, tetanus, poliomyelitis, hepatitis B, infections caused by *Neisseria menin-* gitidis or par *Streptococcus pneumoniae*, chicken pox, mumps, rubella, infections caused by a rotavirus, etc.

According to one embodiment, the PRP-T conjugate is present in powder form, whereas the other antigens are in liquid form, all of the antigens being mixed extemporaneously before administration; according to one alternative embodiment, the vaccine composition is entirely liquid.

The preparation process according to the invention thus makes it possible to prepare a quadrivalent vaccine combination comprising, in addition to the PRP-T conjugate, diphtheria, tetanus and hepatitis B antigens. Alternatively, it makes it possible to prepare a quadrivalent vaccine combination comprising, in addition to the PRP-T conjugate, diphtheria toxoid, tetanus toxoid, and 2 acellular *Bordetella pertussis* antigens (toxoid and filamentous hemagglutinin) or 3 acellular *Bordetella pertussis* antigens (the previous two+pertactin) or else 5 acellular *Bordetella pertussis* antigens (the previous three+the agglutinogens).

It also makes it possible to prepare a pentavalent vaccine combination comprising, in addition to the PRP-T conjugate, diphtheria toxoid, tetanus toxoid, 2, 3 or 5 acellular *Bordetella pertussis* antigens and also inactivated type 1, 2 and 3 polioviruses.

It also makes it possible to prepare a hexavalent vaccine combination comprising, in addition to the PRP-T conjugate, diphtheria toxoid, tetanus toxoid, 2, 3 or 5 acellular *Bordetella pertussis* antigens, hepatitis B and also inactivated type 1, 2 and 3 polioviruses. Such a hexavalent combination can in particular be liquid and can comprise, per 0.5 ml dose:

diphtheria toxoid in amount of 20 IU,
tetanus toxoid in amount of 40 IU,
the hepatitis B surface antigen in a proportion of 10 μg,
pertussis toxoid in a proportion of 25 μg,
pertussis filamentous hemagglutinin in a proportion of 25 μg,
PRP-T in a proportion of 12 μg of PRP,
inactivated type 1, 2 and 3 polioviruses in a respective amount of 40, 8 and 32 DU,
aluminum hydroxide in a proportion of 0.6 mg of $Al^{3+}$.

Alternatively, it makes it possible to prepare vaccine combinations in which the whooping cough antigens consist of the whole *Bordetella pertussis* bacterium.

By virtue of the culture process according to the invention, it is possible to increase the production of Polyribosyl Ribitol Phosphate, without increasing the amount of biomass, thereby making it possible to reduce the amount of contaminating LPSs; this advantage of the process according to the invention is very important to the vaccine industry, where these products are introduced into vaccine compositions as antigens and where the amounts of LPSs must be reduced to a minimum. Having available a process which makes it possible not to increase the amount of LPS produced for a greater amount of PRP offers the possibility of simplifying the subsequent purification process.

Example 1

Preparation of a Culture Medium According to the Invention

A culture medium according to the invention was prepared from a basic medium to which enrichment solutions were added extemporaneously.

The composition of the basic medium is indicated in table I below:

TABLE I

| Compounds | Amounts in mg for 1 l | supplier | product ref. |
|---|---|---|---|
| 60% sodium lactate | 1.5 ml | Prolabo | 27925.292 |
| $K_2HPO_4$ | 300 | VWR Prolabo | 26931.263 |
| $KH_2PO_4$ | 300 | VWR Prolabo | 26923.298 |
| $MgSO_4 \cdot 7H_2O$ | 368 | VWR Prolabo | 25165.260 |
| $Na_2HPO_4 \cdot 12H_2O$ | 28620 | VWR Prolabo | 28028.298 |
| $NaH_2PO_4 \cdot 2H_2O$ | 1870 | VWR Prolabo | 28015.294 |
| L-Arginine | 87 | Sigma | A5006 or A8094 |
| L-Alanine | 134 | Sigma | A7627 or A7469 or A4349 |
| L-Asparagine | 198 | Sigma | A0884 or A7094 |
| L-Lysine | 140 | Sigma | L5626 or L8662 or L7039 |
| L-Glutamine | 220 | Sigma | G3126 or G8540 or G5792 |
| L-Histidine | 78 | Sigma | H8000 or H6034 or H3911 |
| L-Tryptophan | 200 | Sigma | T0254 or T8941 or T4196 |
| L-Valine | 115 | Sigma | V0500 or V0513 or V4638 |
| L-Isoleucine | 130 | Sigma | I2752 or I7403 or I5281 |
| L-Leucine | 130 | Sigma | L8000 or L6914 or L8912 |
| L-Tyrosine | 180 | Sigma | T3754 or T8566 or T4321 |
| L-Phenylalanine | 165 | Sigma | P5482 |
| L-Cystine | 61 | Sigma | C8755 or C7602 or C5735 |
| L-aspartic acid | 1065 | Sigma | A9256 or A5474 |
| L-glutamic acid | 1471 | Sigma | G1251 or G8415 |
| Pyridoxine HCl | 4 | Sigma | P5669 |
| Riboflavin | 0.2 | Sigma | R4500 |
| Thiamine HCl | 4 | Sigma | T4625 |
| Biotin | 4 | Sigma | B4501 |
| Ca Pantothenate | 4.5 | Sigma | P5710 |
| Uracil | 70 | Sigma | U0750 |
| Hypoxanthine | 20 | Sigma | H9377 |
| $FeSO_4 \cdot 7H_2O$ | 2.5 | Aldrich | 450278 |
| $ZnSO_4 \cdot 7H_2O$ | 5 | Sigma | Z4750 |
| $CoCl_2 \cdot 6H_2O$ | 1 | Fluka | 60818 |
| $MnSO_4 \cdot H_2O$ | 5 | Sigma | M7634 |
| $CaCl_2 \cdot 2H_2O$ | 13 | Panreac | 131232.1211 |

To prepare 1 liter of medium, the various compounds were added, in the order described in the table above, to approximately 100 ml of demineralized water, with stirring using a magnetic bar. Before addition, all the powders had been previously dissolved in a small volume of demineralized water with, in certain cases, the addition of acid or of base. Thus, for the valine, isoleucine and leucine, it was necessary to add, to the amounts indicated in the table, 140 μl of 10 N KOH; to the tyrosine, it was necessary to add 280

μl of 10 N KOH; to the phenylalanine, it was necessary to add 210 μl of 37% HCl, and to the cystine, it was necessary to add 70 μl of 37% HCl.

Finally, the pH was adjusted to 7.2±0.1 with 10 N KOH (in the event of the pH having been too high, 37% HCl would have been used), then demineralized water was used to make the volume up to the desired amount.

The medium was then sterilized by means of filtration on a filter having a cut-off threshold at 0.22 μm.

It was thus possible to store the medium for 72 hours at 5° C.

Before the inoculation of the medium, the following were added:
- 27.3 ml of glucose at 512.8 g/l prepared from anhydrous D(+) glucose supplied by the company VWR under the reference 24379.294,
- 5 ml of a solution of NAD at 1 g/l, supplied by the company Sigma under the name β-Nicotinamide Adenine Dinucleotide hydrate (ref. 43410),
- 4 ml of a stock solution comprising protoporphyrin at the concentration of 0.25 g/l and ammonium hydroxide at the concentration of 5 ml/l; the protoporphyrin being supplied by the company Sigma Aldrich under the name Protoporphyrin IX disodium salt (ref. 258385) and the ammonium hydroxide by the company VWR under the name Ammonia solution 28% (ref. 21190.292), in order to obtain 1 liter of medium ready to be inoculated, and comprising, in addition to the elements described in table I above, the following additional elements with the concentrations as indicated in table II below:

TABLE II

| Compounds | Concentration before inoculation in the medium |
|---|---|
| Protoporphyrin | 1 mg/l |
| Aqueous ammonia | 17.7 μg/l |
| Anhydrous glucose | 14 g/l |
| NAD | 5 mg/l |

Example 2

Preparation of a Culture Medium According to the Prior Art

A culture medium according to the prior art was prepared by adding specific enrichment solutions to a basic medium.

The composition of the basic medium is indicated in table III below:

TABLE III

| Compounds | Concentration in the basic medium |
|---|---|
| Pea peptone | 7.42 g/l |
| 60% Sodium Lactate | 1.5 ml/l |
| $Na_2HPO_4 \cdot 12H_2O$ | 31.14 g/l |
| $NaH_2PO_4 \cdot 2H_2O$ | 2.03 g/l |
| Cystine (L) | 0.07 g/l |
| HCl (10N) | 0.07 ml/l |
| Tryptophan (L) | 0.02 g/l |
| $(NH_4)_2SO_4$ | 1 g/l |
| $MgSO_4 \cdot 7H_2O$ | 0.4 g/l |
| $CaCl_2 \cdot 2H_2O$ | 0.02 g/l |

To prepare this basic medium, each of the elements was added, in the order in which they are indicated in the table, to 100 ml of demineralized water continuously stirred using a magnetic bar. Each of the elements, supplied in powder form, had previously been dissolved in a small volume of demineralized water.

The pea peptone comes from the company Kerry and is sold under the reference Hy-pea 7404. The $(NH_4)_2SO_4$ is supplied by the company VWR under the reference 21333.296. The other elements come from the same suppliers and are supplied under the same references as those described in example 1 for the preparation of the medium according to the invention.

The final pH was adjusted to 7.2±0.1 with 10 N KOH (in the event of the pH having been too high, 37% HCl would have been used).

Demineralized water was then added in order to obtain the desired volume, and then it was sterilized by autoclaving, according to a cycle of 30 minutes at 120° C.

Once sterilized, the medium could be stored for 15 days at 4° C.

The enrichment solutions A, B, C and D were added to this basic medium.

The solution A is a solution comprising anhydrous glucose at the concentration of 512.8 g/l, supplied by the company VWR under the name anhydrous D(+) glucose (ref. 24379.294).

The solution B is a stock solution comprising NAD at the concentration of 1 g/l, supplied by the company Sigma under the name β-Nicotinamide Adenine Dinucleotide hydrate (ref. 43410).

The solution C is a stock solution comprising protoporphyrin at the concentration of 0.25 g/l and ammonium hydroxide at the concentration of 5 ml/l; the protoporphyrin being supplied by the company Sigma Aldrich under the name Protoporphyrin IX disodium salt (ref. 258385) and the ammonium hydroxide by the company VWR under the name Ammonia solution 28% (ref. 21190.292).

The solution D is a concentrated solution comprising autolytic yeast extract ultrafiltrate (Ufel) at 125 g/l; it is supplied by the company Biospringer under the name Ultrafiltrat d'extrait autolytique de levure (Ufel) [Autolytic yeast extract ultrafiltrate] (Ref. springer 0701).

Each of these solutions is sterilized by filtration on a filter of which the cut-off threshold is 0.22 μm.

The following were added to 1 liter of basic medium:
- 35.1 ml of solution A
- 5 ml of solution B
- 4 ml of solution C
- 40 ml of solution D.

The addition of each of the solutions to the basic medium was carried out under a laminar flow hood and resulted in a culture medium having, before inoculation, in addition to the elements mentioned in table III above, the following additional elements in the concentration indicated in table IV below:

TABLE IV

| Compounds | Concentration before inoculation in the medium |
|---|---|
| Autolytic yeast extract ultrafiltrate (Ufel) | 4.9 g/l |
| Protoporphyrin | 1 mg/l |
| Aqueous ammonia | 17.7 μg/l |
| Anhydrous glucose | 18 g/l |
| NAD | 5 mg/l |

Example 3

Comparison of PRP Production with a Medium According to the Invention as Described in Example 1 and a Medium of the Prior Art as Described in Example 2

These comparative experiments were carried out according to a 2-step culture protocol:

a step of preculture in a non-baffled 1-liter glass Erlenmeyer flask, at 36° C. with stirring at 130 rpm (revolutions per minute), for a period of 8 hours, at the end of which the strain is at the end of the linear growth phase; this preculture is initiated by inoculating 280 ml of culture medium with an inoculum of bacteria of *Haemophilus influenzae* type b containing at least 2 copies of the cap locus, at a concentration of 0.5% (volume/volume);

then a transfer of 90 ml of the preculture made it possible to inoculate a 2-liter Biostat B plus fermentor containing 1.8 liters of culture medium. This fermentor was maintained at 37° C., with stirring at 400 rpm, with an aeration of 0.45 lpm (liter per minute) for 12 hours.

After 12 hours of culture, the O.D. at 694 nm was measured, which made it possible to determine the biomass. This is because, during previous tests, it was possible to determine that one unit of optical density measured at 694 nm corresponded to 0.64 g of biomass (dry mass)/liter.

The amount of total PRP in the culture supernatant was determined by high-performance anion exchange chromatography with pulsed amperometric detection (HPAEC-PAD), according to a method very similar to that described in the publication by Sturgess et al. (Vaccine 17 (1999) 1169-1178). The culture supernatant was filtered by passing it through a 0.22 μm filter, and then 500 μl of supernatant were ultrafiltered via the use of Amicon ultra columns with a cut-off threshold of 10 kDa (Millipore ref. UFC5010BK) and then subjected to a basic hydrolysis step by adding NaOH.

The hydrolysis was carried out at ambient temperature for a minimum of 4 hours. The validity of the assay was controlled by using an internal standard, glucosamine-1-phosphate (GlcN1P), present in the hydrolysis solution, and by regularly passing through an internal control having a known PRP concentration. With respect to the indications of Sturgess et al, the mobile phase was composed of 35 mM NaOH and 114 mM $CH_3COONa$ and the regeneration phase was carried out for 10 minutes with 100 mM NaOH and 400 mM $CH_3COONa$.

The results obtained are indicated in table V below:

TABLE V

|  | Medium according to the invention (4 tests) | Medium of the prior art (1 test) |
| --- | --- | --- |
| O.D. at 694 nm | 2.52 ± 0.14 | 3.9 |
| Biomass in g of dry mass/liter of culture medium | 1.74 ± 0.09 | 2.6 |
| PRP concentration in mg/liter of culture medium | 349 ± 22 | 169 |
| Specific production in mg of PRP/g of biomass | 199 ± 3 | 66 |

These results show the advantage of the process according to the invention for the PRP productivity: it is in fact noted that, for the same volume of culture medium, while the biomass obtained was greater with a culture medium according to the prior art, the amount of PRP was, on the other hand, smaller.

Example 4

Comparison of the Amount of PRP and of LPS Present in a Culture Supernatant According to the Process of the Invention, and in a Culture Supernatant According to a Process of the Prior Art The culturing of *Haemophilus influenzae* type b was carried out comparatively with a medium according to the invention and with a medium according to the prior art, in the manner described in example 3, with however the difference that the basic medium of the process according to the prior art comprised 10 g/l of casein acid hydrolysate supplied by the company Solabia (ref. A1434) in place of the pea peptone present in the medium according to example 3.

The preculture time is, as in example 3, 8 hours, and the culture time is 12 hours. The assaying of PRP and the assaying of LPS are both carried out by HPAEC-PAD; but the assaying of LPS is carried out by quantification of a particular monosaccharide, heptose, using a standard range of purified LPS having undergone the same protocol, the internal control for this assay being rhamnose.

The results obtained are indicated in table VI below:

TABLE VI

|  | Medium according to the invention (4 tests) | Medium according to the prior art (3 tests) |
| --- | --- | --- |
| OD at 694 nm | 2.5 ± 0.1 | 3.9 ± 0.3 |
| Biomass in g of dry mass/l of medium | 1.7 ± 0.1 | 2.5 ± 0.2 |
| LPS concentration in mg/l of medium | 5 ± 1 | 4.6 ± 1 |
| PRP concentration in mg/l of medium | 349 ± 22 | 17 ± 5 |
| PRP/LPS ratio | 74 ± 15 | 38 ± 6 |

The results obtained show the advantage of the process according to the invention, which makes it possible to reduce the amount of LPSs produced relative to the amount of PRP.

This represents a significant advantage of the process according to the invention, since this very much simplifies the purification operations, while at the same time maintaining an appropriate safety level.

Example 5

Test for Evaluating the Importance of Zinc

The importance of the presence of zinc in the culture medium was studied.

To this effect, 3 media were compared:

a medium such as that described in example 1, called MS, a medium which has a composition identical to that of example 1, but without the $ZnSO_4$, called MS Zn—, a medium such as that described in example 1, but with a $ZnSO_4$ concentration which is 4 times higher, i.e. 20 mg/l, said medium being called MS Zn++.

The media were then sterilized by means of filtration on a filter having a cut-off threshold at 0.22 μm.

A step of preculture in a non-baffled 1-liter glass Erlenmeyer flask was first of all performed, for 16 hours at 36° C. with stirring at 130 rpm, by inoculating 280 ml of a medium as described in example 4 with a frozen sample of *Haemophilus influenzae* type b bacteria having in the genetic code thereof at least 2 copies of the cap locus. 9.5 ml of preculture were then washed in each of the culture media to be tested, before the inoculation for the culture which was performed each time in a baffled 500 ml polycarbonate Erlenmeyer flask containing 170 ml of the culture medium to be tested; the culture was performed for 12 hours at 37° C. and stirring was performed at 150 rpm.

For each medium, the biomass, the PRP concentration and also the amount of LPS at the end of culture were determined, in the same way as described in examples 3 and 4, and the PRP/biomass and also LPS/biomass and PRP/LPS ratios were calculated.

The results obtained are indicated in table VII below:

TABLE VII

|  | MS | MS Zn− | MS Zn++ |
|---|---|---|---|
| Biomass in g of dry mass/liter of culture medium | 1.98 | 1.23 | 2.22 |
| PRP concentration in mg/liter of culture medium | 319 | 203 | 372 |
| Specific production in mg of PRP/g of biomass | 160 | 165 | 167 |
| LPS concentration in mg/liter of culture medium | 11.5 | 8.8 | 12.1 |
| LPS/biomass ratio in mg/g of biomass | 6.1 | 7.2 | 5.5 |
| PRP/LPS ratio in mg/mg | 30 | 23 | 31 |

These results showed that the presence of zinc in the culture medium makes it possible to significantly increase the production of biomass and also the production of PRP, without, however, proportionally increasing the amount of LPS Example 6

Tests in a 5-Liter Fermentor

The culturing of *Haemophilus influenzae* type b was carried out in the culture medium described according to the invention in example 1, using only products guaranteed by the suppliers to be animal-free and using synthetic protoporphyrin as described in patent application FR 2 914 302, and supplied by the company Solvias AG under the name: Protoporphyrin IX Disodium Salt (Ref. SOL20402). The tests were then carried out in the manner described in example 3, with the exception that the fermentors used were 5-liter fermentors regulated at 37° C., with stirring at 550 rpm and aeration at 0.5 lpm. The inoculum volume was then 280 ml, i.e. the entire preculture Erlenmeyer flask.

The PRP and LPS concentration was determined according to the protocols described in examples 3 and 4.

The results obtained are indicated in table VIII below:

TABLE VIII

|  | Animal-free medium according to the invention |
|---|---|
| O.D. at 694 nm | 3.58 |
| Biomass in g of dry mass/l of medium | 2.29 |

TABLE VIII-continued

|  | Animal-free medium according to the invention |
|---|---|
| PRP concentration in mg/l of medium | 567 |
| Specific production in mg of PRP/g of biomass | 247 |

These results confirm the previous results, and show the advantage of the process according to the invention for obtaining a large amount of PRP.

Example 7

Comparison of the Production of Biomass and of PRP with a Medium According to the Invention as Described in Example 1 and with Chemically Defined Media Described in the Prior Art The culturing of *Haemophilus influenzae* type b was carried out in the culture medium described according to the invention in example 1 and also in 8 media described in publications in connection with the culture of *Haemophilus influenzae*, and presented as being chemically defined.

These 8 media were prepared according to the recommendations of the authors. They are, in chronological order, the media of:

Talmadge and Herriott: Biochemical and Biophysical Research Communications, (March 1960), Vol. 2 N°3, p 203-206), Butler: J. gen. Microbiol. (1962), 27, 51-60, Wolin: J. Bacteriol. Vol. 85, (1963) Notes, p 253-254, Herriott et al.: Journal of Bacteriology, (February 1970), Vol. 101, N°2, 513-516, Klein and Luginbuhl: Journal of General Microbiology (1979), 113, 409-411

Coleman et al.: Journal of Clinical Microbiology, (September 2003), Vol. 41, N°9 p. 4408-4410.

The references of the products used to prepare these 8 media are reproduced in table IX below:

TABLE IX

| Products | Suppliers | product ref. |
|---|---|---|
| Uridine | Sigma | U3003 |
| Inosine | Sigma | I4125 |
| Adenosine | Sigma | A4036 |
| Guanine | Sigma | G6779 |
| Guanosine | Sigma | G6264 |
| Vitamine B12 | Sigma | V2876 |
| Citrulline | Sigma | C7629 |
| Choline chloride | Fluka | 26978 |
| Thimidine | Sigma | T9250 |
| Inositol | Sigma | I5125 |
| Putrescine dihydrochloride | Sigma | P5780 |
| Nicotinamide | Sigma | N0636 |
| Porcine hematin | Sigma | H3281 |
| Hemin | Fluka | 51280 |
| Sodium oleate | Sigma | O7501 |
| Sodium acetate | Fluka | 71185 |
| Folic acid | Sigma | F7876 |
| Polyvinyl alcohol | Sigma | 341584 |
| Triethanolamine | Sigma | 90278 |
| Glycylglycine buffer | Libios | B-GLYGLY250 |
| Tween 40 | Sigma | P1504 |
| Tween 80 | Sigma | P1754 |
| Tris buffer | VWR | 33621.260 |
| ethylenediaminetetraacetate | VWR | 20302.180 |
| HEPES | Sigma | H3375 |
| Glutathione | Sigma | G6013 |

TABLE IX-continued

| Products | Suppliers | product ref. |
|---|---|---|
| Adenine | Sigma | A8626 |
| Proline | Sigma | P0380 |
| Threonine | Sigma | T8625 |
| Glycine | Sigma | G7126 |
| Methionine | Sigma | M9625 |
| Serine | Sigma | S4500 |
| Glycerol | VWR | 24387.292 |
| $K_2SO_4$ | VWR | 26994.293 |
| KCl | VWR | 26764.298 |
| $MgCl_2 \cdot 6H_2O$ | Panreac | 131396.1211 |
| NaCl | VWR | 27810.295 |
| $NaHCO_3$ | VWR | 27778.260 |
| $NH_4Cl$ | VWR | 21236.291 |
| RPMI 1640 with L-glutamine and 25 mM HEPES | Invitrogen | former ref. cited in the publication by Coleman (2003) ref. 61870036 => new ref. 52400025 |
| Sodium pyruvate MEM 100 mM | Invitrogen | former ref. cited in the publication by Coleman (2003) ref. 11360070 => new ref. 11360039 |

The media were then sterilized by means of filtration on a filter having a cut-off threshold at 0.22 μm.

A step of preculture in a non-baffled 1-liter glass Erlenmeyer flask was first of all carried out, for 16 hours at 36° C. with stirring at 130 rpm, by inoculating 280 ml of a medium as described in example 4 with a frozen sample of *Haemophilus influenzae* type b bacteria having in the genetic code thereof at least 2 copies of the cap locus. 9.5 ml of preculture were then washed in each of the culture media to be tested, before the inoculation for the culture which was performed each time in a baffled 500 ml polycarbonate Erlenmeyer flask containing 170 ml of the culture medium to be tested; the culture was performed for 12 hours at 37° C. and stirring at 150 rpm.

Each test was carried out at least 3 times.

For each medium, each hour, the O.D. at 694 nm was measured and the PRP concentration was determined at the end of culture, in the same way as described in example 3.

The O.D. results are reproduced in FIG. 1.

The results of the PRP determinations are indicated in table X below:

TABLE X

| at 12 h | O.D. at 694 nm | PRP (mg/l) |
|---|---|---|
| Medium according to the invention | 2.86 ± 0.12 | 320 ± 15 |
| Talmadge | 0.28 ± 0.10 | 20 ± 1 |
| Butler | 0.04 ± 0.00 | 2 ± 0 |
| Wolin | 0.04 ± 0.00 | 6 ± 0 |
| Herriot Mic-cit | 1.26 ± 0.15 | 138 ± 7 |
| Herriot Mic | 0.98 ± 0.13 | 101 ± 5 |
| Klein MMA (cit) | 0.38 ± 0.01 | 40 ± 2 |
| Klein MMB | 0.20 ± 0.03 | 27 ± 1 |
| Coleman | 1.43 ± 0.04 | 204 ± 10 |

Example 8

Industrial-Scale PRP Production (1000 Liters)

A culture medium according to the invention having the composition of example 1, except for the zinc, where the concentration is 20 mg/l instead of 5 mg/l, was prepared. This is because example 5 showed that this concentration made it possible to produce more PRP without increasing the amount of LPS.

The medium was identical for the precultures and the final culture, except the pH (initial pH 7.2±0.1, then free pH for the precultures and pH regulated at 6.7±0.1 for the production culture).

The medium was prepared as in example 1. After having mixed the compounds previously dissolved in a small volume of purified water, with, in certain cases, the addition of acid or of base (cf. example 1), and before adding the sufficient quantity of purified water, the pH was adjusted to 7.2±0.1 for the precultures and 6.7±0.1 for the final culture (with 10 N potassium hydroxide or sodium hydroxide or 37% HCl).

The medium was then sterilized by means of filtration on a filter having a cut-off threshold at 0.22 μm.

It was thus possible to store the medium for 72 hours at 5° C.

Before the inoculation of the medium, the following were added:
  glucose at 512.8 g/l prepared from anhydrous D(+) glucose supplied by the company VWR under the reference 24379.294,
  a solution of NAD at 1 g/l, supplied by the company Sigma under the name β-Nicotinamide Adenine Dinucleotide hydrate (ref. 43410),
  a stock solution comprising protoporphyrin at the concentration of 0.25 g/l and ammonium hydroxide at the concentration of 5 ml/l; the protoporphyrin being supplied by the company Solvias AG under the name Protoporphyrin IX disodium salt (ref. SOL20402) and the ammonium hydroxide by the company VWR under the name Ammonia solution 28% (ref. 21190.292),
in order to obtain a medium ready to be inoculated, and comprising, in addition to the elements described in table I of example 1, the additional elements with the concentrations as indicated in table II of example 1 (except the glucose at a final concentration of 14.87 g/l instead of 14 g/l).

The 1000-liter scale process comprised a series of 3 precultures:
  the first precultures were performed in a non-baffled 1-liter Erlenmeyer flask containing 290 ml of complete culture medium, at 37° C. with stirring at 130 rpm (revolutions per minute), for a period of 17-18 hours. These precultures were initiated by inoculating the culture medium with an inoculum of *Haemophilus influenzae* type b bacteria containing at least 2 copies of the cap locus, with an inoculation level corresponding to an initial target $OD_{694\ nm}$ of 0.014;
  the second preculture series was performed in a 6.8-liter fermentor. Two fermentors containing 5.2 liters of complete culture medium were each inoculated with 260 ml of a preculture of series 1. These fermentors were maintained for 4 hours at 37° C.±1, with an initial pH at 7.2±0.2, a $pO_2$ maintained at 30% with a cascade involving an increase in the stirring (500 to 800 rpm), then an increase in the aeration (0.5 to 2.5 lpm) and then a flow rate of pure $O_2$ between 0 and 6 lpm;
  the third preculture series was performed in a 120-liter fermentor containing 57 liters of complete medium which was inoculated with 5.8 liters of the preculture originating from series 2. This fermentor was maintained for 3 hours 10 at 37° C.±1, with an initial pH of 7.2±0.2, a $pO_2$ maintained at 30% with a cascade involving an increase in the stirring (300 to 425 rpm), then an increase in the aeration (6 to 28 lpm) and then a flow rate of pure $O_2$ between 0 and 50 lpm.

The industrial culture was performed in a 1000-liter fermentor containing 778 liters of complete medium which was inoculated with 39 liters of a preculture of series 3. This fermentor was maintained at 32° C.±1, with a pH regulated at 6.7±0.2 (with a 2.5 N sodium hydroxide solution), a $pO_2$ maintained at 70% by virtue of a cascade involving an increase in the stirring (100 to 230 rpm), then an increase in the aeration (70 to 150 lpm) and then a flow rate of pure $O_2$ between 0 and 500 lpm. Moreover, antifoam (Biospumex at 4%) was added on demand depending on the foam level.

After 12 hours of culture, the O.D. at 694 nm was measured, which made it possible to determine the biomass (according to the correspondence of one OD unit corresponding to 0.64 g of dry biomass). The PRP and LPS concentration was determined according to the protocols described in examples 3 and 4.

The results obtained are indicated in table XI below:

TABLE XI

| | Medium according to the invention (1 test) |
|---|---|
| O.D. at 694 nm | 3.45 |
| Biomass in g of dry mass/liter of culture medium | 2.21 |
| PRP concentration in mg/liter of culture medium | 865 |
| Specific production in mg of PRP/g of biomass | 392 |
| LPS concentration in mg/liter of culture medium | 35.6 |
| LPS/biomass ratio in mg/g of biomass | 16.1 |
| PRP/LPS ratio in mg/mg | 24.3 |

These results showed the advantage of the process according to the invention for the PRP productivity and the PRP/LPS ratio, said results having been demonstrated on an industrial scale.

The invention claimed is:

1. A process for producing, on an industrial scale, capsular polysaccharide of *Haemophilus influenzae* type b (PRP) suitable for use in a vaccine, the process comprising culturing a strain of *Haemophilus influenzae* type b (Hib) in a culture medium, and harvesting and treating supernatant from the culture medium to extract the capsular polysaccharide therefrom, said culture medium comprising at least:
   a source of carbon,
   a protoporphyrin,
   salts,
   amino acids,
   NAD or NADH,
   vitamins,
   pH-regulating means, and
   zinc,
   wherein said culture medium is chemically defined.

2. The process as claimed in claim 1, wherein said pH-regulating means consist of buffer salts.

3. The process as claimed in claim 1, wherein said source of carbon is glucose, fructose, galactose, glycerol, xylose, ribose, fucose, sialic acid, lactate, or a combination thereof.

4. The process as claimed in claim 1, wherein said protoporphyrin is synthetic protoporphyrin IX.

5. The process as claimed in claim 1, wherein said salts are chosen from potassium, magnesium, sodium, calcium, iron, zinc, cobalt and manganese salts.

6. The process as claimed in claim 1, wherein said salts are chosen from: $K_2HPO_4$; $KH_2PO_4$; $MgSO_4.7\ H_2O$; $Na_2HPO_4.12H_2O$; $NaH_2PO_4.2H_2O$; $CaCl_2.2H_2O$; $FeSO_4.7H_2O$; $ZnSO_4.7H_2O$; $CoCl_2.6H_2O$; and $MnSO_4.H_2O$.

7. The process as claimed in claim 1, wherein the composition comprises:
   arginine or citrulline,
   alanine,
   histidine,
   tryptophan,
   tyrosine,
   phenylalanine,
   at least one of cystine, cysteine, or glutathione, and
   at least one of asparagine, glutamine, aspartic acid, or glutamic acid.

8. The process as claimed in claim 1, wherein said culture medium comprises at least arginine, alanine, histidine, tryptophan, tyrosine, phenylalanine, cystine, aspartic acid and glutamic acid.

9. The process as claimed in claim 7, wherein the at least one of cysteine, cysteine, or glutathione is glutathione or cysteine.

10. The process as claimed in claim 1, wherein said vitamins are chosen from: thiamine, pantothenate, uracil, hypoxanthine, biotin, riboflavin and pyridoxine.

11. The process as claimed in claim 7, wherein the arginine or citrulline is citrulline.

12. The process as claimed in claim 1, further comprising conjugating the capsular polysaccharide obtained to a carrier protein.

13. The process as claimed in claim 12, wherein the carrier protein is tetanus toxoid.

14. A process for preparing a vaccine composition, the process comprising
   a) preparing an antigen against *Haemophilus influenzae* type b (Hib) according to the method of claim 1,
   b) conjugating the capsular polysaccharide obtained in a) to a carrier protein,
   c) combining the conjugate obtained in b) with at least one or more antigens suitable for use in a pediatric vaccine.

15. The process for preparing a vaccine composition as claimed in claim 14, wherein the conjugate obtained in b) is combined with diphtheria, tetanus and hepatitis B antigens.

16. The process for preparing a vaccine composition as claimed in claim 14, wherein the conjugate obtained in b) is combined with diphtheria toxoid, tetanus toxoid, and acellular *Bordetella pertussis* antigens toxoid and filamentous hemagglutinin.

17. The process for preparing a vaccine composition as claimed in claim 14, wherein the conjugate obtained in b) is combined with diphtheria toxoid, tetanus toxoid, and acellular *Bordetella pertussis* antigens toxoid, pertactin and filamentous hemagglutinin.

18. The process for preparing a vaccine composition as claimed in claim 14, wherein the conjugate obtained in b) is combined with diphtheria toxoid, tetanus toxoid, and acellular *Bordetella pertussis* antigens toxoid, pertactin, agglutinogens and filamentous hemagglutinin.

19. The process for preparing a vaccine composition as claimed in claim 14, wherein the conjugate obtained in b) is combined with diphtheria toxoid, tetanus toxoid, 2, 3 or 5 acellular *Bordetella pertussis* antigens and also inactivated type 1, 2 and 3 polioviruses.

20. The process for preparing a vaccine composition as claimed in claim 14, wherein the conjugate obtained in b) is combined with diphtheria toxoid, tetanus toxoid, hepatitis B, 2, 3 or 5 acellular *Bordetella pertussis* antigens and also inactivated type 1, 2 and 3 polioviruses.

21. The process for preparing a vaccine composition as claimed in claim 14, wherein the conjugate obtained in b) is combined with the whole *Bordetella pertussis* bacterium.

22. The process as claimed in claim 7 wherein the culture medium further comprises one or more of lysine, valine, isoleucine, and leucine, and phenylalanine.

23. The process as claimed in claim 1 wherein the culture medium comprises at least thiamine, pantothenate, uracil or citrulline, hypoxanthine, biotin, riboflavin, and pyridoxine.

24. The process as claimed in claim 1, wherein said vitamins are chosen from thiamine, pantothenate, citrulline, hypoxanthine, biotin, riboflavin and pyridoxine.

25. The process according to claim 14 wherein the one or more antigens are selected from antigens suitable for use in vaccination against diphtheria, tetanus, polio, hepatitis B, chicken pox, mumps, rubella, infections caused by *Neisseria meningitides* or *Streptococcus pneumoniae*, or infections caused by rotavirus.

26. The process according to claim 14, wherein the conjugate obtained in c) is combined with at least one or more antigens against diphtheria, tetanus, poliomyelitis, hepatitis B, infections caused by *Neisseria meningitides* or by *Streptococcus pneumonia.*

* * * * *